United States Patent [19]

Gibilsco

[11] Patent Number: 5,221,027
[45] Date of Patent: Jun. 22, 1993

[54] FLUID DISPENSER TIP WITH RECESSED DISPENSING NOZZLE

[75] Inventor: Kenneth J. Gibilsco, Coopersburg, Pa.

[73] Assignee: Merck & Co., Inc., Rahway, N.J.

[21] Appl. No.: 785,640

[22] Filed: Oct. 31, 1991

Related U.S. Application Data

[63] Continuation-in-part of Ser. No. 657,904, Oct. 31, 1991, abandoned.

[51] Int. Cl.$^5$ .............................................. B65D 47/18
[52] U.S. Cl. ................................... 222/420; 222/567; 604/302
[58] Field of Search ............... 222/108, 420, 402.12, 222/567, 568, 570; 604/295, 302, 294, 300, 301

[56] References Cited

U.S. PATENT DOCUMENTS

| | | | |
|---|---|---|---|
| D. 30,756 | 5/1899 | Stephens . | |
| D. 244,670 | 6/1977 | Winikoff | D9/261 |
| D. 293,474 | 12/1987 | Jermyn | D24/66 |
| 1,077,707 | 11/1913 | Hartman | 222/108 |
| 1,750,530 | 3/1930 | La Paugh et al. | 604/301 |
| 2,087,139 | 7/1937 | Cameron | 221/80 |
| 2,482,431 | 9/1949 | Okawa | 128/233 |
| 2,516,818 | 7/1950 | West | 128/249 |
| 2,898,911 | 8/1959 | Taylor | 128/249 |
| 3,016,898 | 1/1962 | Erwin | 128/249 |
| 3,439,843 | 4/1969 | Corsette | 222/568 |
| 3,872,865 | 3/1975 | Casey | 128/233 |
| 3,888,251 | 6/1975 | Harrison | 128/233 |
| 3,913,842 | 10/1975 | Singer | 239/337 |
| 3,917,119 | 11/1975 | Kahn | 222/108 |
| 3,945,381 | 3/1976 | Silver | 128/249 |
| 4,002,168 | 1/1977 | Petterson | 128/233 |
| 4,111,200 | 9/1978 | Sbarra et al. | 128/233 |
| 4,701,167 | 10/1987 | Chekan | 604/310 |
| 4,733,802 | 3/1988 | Sheldon | 222/181 |
| 4,834,728 | 5/1989 | McKenna | 604/301 |
| 4,960,407 | 10/1990 | Cope | 604/300 |
| 5,007,905 | 4/1991 | Bauer | 604/295 |
| 5,037,406 | 8/1991 | Smith et al. | 222/568 X |
| 5,074,440 | 12/1991 | Clements et al. | 222/213 X |

FOREIGN PATENT DOCUMENTS

| | | |
|---|---|---|
| 85811/75 | 4/1977 | Australia . |
| 68247/87 | 10/1987 | Australia . |
| 2723617 | 11/1978 | Fed. Rep. of Germany . |
| 722852 | 9/1931 | France . |
| 1008118 | 5/1952 | France ........................... 222/420 |
| 2579459 | 10/1986 | France . |
| 1163903 | 9/1969 | United Kingdom . |
| 1515027 | 6/1978 | United Kingdom . |
| 2142829 | 1/1985 | United Kingdom . |

OTHER PUBLICATIONS

G. Hovding and H. Sjursen, *Acta Ophthalmologica*, 60, 213 (1982).

A. J. Winfield, et al., *British J. Ophthalmology*, 74, 477 (1990).

*Primary Examiner*—Andres Kashnikow
*Assistant Examiner*—Kenneth Bomberg
*Attorney, Agent, or Firm*—William H. Nicholson; Joseph F. DiPrima

[57] ABSTRACT

A dropper nozzle is combined with a shield member to form a dropper tip which prevents inadvertent contact of the nozzle during manufacture and use, thereby preventing damage to, or contamination of the nozzle and the contents of the dropper bottle to which the nozzle is attached. The shield is small and is intended to protect the nozzle from coming in contact with the eye, or any part of the face, and not particularly to aid in positioning or directing the drop.

1 Claim, 4 Drawing Sheets

FLUID DISPENSER TIP WITH RECESSED DISPENSING NOZZLE

This application is a continuation-in-part of U.S. Ser. No. 07/657,904 filed Oct. 31, 1991, now abandoned.

BACKGROUND OF THE INVENTION

This invention relates to a dropper tip for fluid dispensing devices in which it is desired to keep the nozzle from coming in contact with other surfaces, which may contaminate or damage the nozzle. In particular it relates to a dropper tip for the delivery of fluids to the eye. This device is not intended to come in contact with the eye, or any part of the face, or particularly to aid in positioning or directing the drop.

A significant problem with previous devices for dispensing ophthalmic solutions is contamination of the dropper nozzle by inadvertent contact with the eye and other surfaces. The problem is described in G. Hovding and H. Sjursen, Acta Opthalmologica, 60, 1982, pp. 213–222. This contact also can clog the orifice of the tip, making it impossible to dispense further drops. Contamination of the nozzle can then result in microbial contamination of the solution remaining in the dropper bottle and the transfer of this contamination to either or both eyes.

One common route of this contamination comprises touching the dropper nozzle to the eye during administration of medication. The touching permits contamination of the fluid remaining in the nozzle, which liquid ultimately flows back into the dropper bottle, contaminating the entire contents.

Some devices have been reported which serve to prevent contact of a dropper nozzle but which were designed primarily to aid in aiming the dropper nozzle properly. See for example U.S. Pat. Nos. 4,834,728; 3,945,381; 4,111,200 and 4,733,802. These devices generally comprise a large cup-shaped or cone-shaped member, the rim of which rests on the patient's face over the eye socket and have a tip composed of a nozzle protruding through the cup-shaped member oriented so that drops from the nozzle would enter the eye.

These reported devices are fairly large, cumbersome and not easily carried in a handbag or pocket. The diameter of the cup-shaped member is large, larger than the diameter of the human eye. This diameter is large enough to permit easy contact of the dropper tip with fingers or other septic objects resulting in contamination of the device and its contents. Furthermore, covering of the eye with the large cup-shaped member may actually increase the blink reflex, thus raising the likelihood that the drop will miss the intended target.

Now, with the novel dropper tip of this invention, there is provided a dropper tip consisting of a nozzle in combination with a small shield member wherein the dispensing end of the dropper nozzle is recessed within the confines of the shield. The shield may be an integral part of the dropper tip or the shield may be separate and added to or removed from the existing nozzle or dispensing device.

The shield is small, with a diameter of ¼ inch to 1 inch, not to exceed the diameter of the eye. In the case where the invention consists of a plurality of fingers or two fingers joined to form a portion of the cup or thimble-shaped shield, the diameter is that of the circle which would be formed by joining the fingers. The shield is not intended to come in contact with the eye or with any part of the face. Preferably, the shield has a diameter of ¼ inch to ⅜ inch.

In one class of embodiments of this invention the shield is an integral part of the dropper tip. The shield cannot be added or removed and, therefore, must always be used. In this class of embodiments, the dropper tip itself includes as a part of the whole a member which prevents nozzle contact with the eye or other surface. In addition, the device is small and easily manufactured.

The dropper tip of this invention may also consist of a shield that can be added to or removed from an existing dispensing device. The shield can be designed to accommodate the dimensions of existing bottles for dispensing ophthalmic solutions. The embodiments of this second class are easily and cheaply manufactured.

In the course of manufacturing the finished product, a dispenser filled with fluid, the nozzles of existing devices for dispensing ophthalmic solutions are often damaged, resulting in leaking dispensers which cannot be used to administer drops accurately. By its design, the recessed tip of the device of this invention is protected from becoming damaged in the process of manufacturing and filling.

DESCRIPTION OF THE INVENTION

The present invention relates to a dropper tip comprising a nozzle and a shield member of a device for the dropwise dispensing of fluids, wherein the dispensing end of the nozzle is recessed below the confines of the shield member; the shield member being sufficiently close to the dispensing end of the nozzle to prevent contact of the dispensing end of the nozzle with external surfaces, specifically to prevent contact of the dispensing end of the nozzle with the eye.

The nozzle of the novel dropper tip is the functional equivalent of the nozzle of known, marketed dispensing devices.

The shield member of the novel dropper tip is designed so that, when attached to the dispensing device, if the dropper tip were to approach a surface, the nozzle of the dropper tip would be protected from contact with the surface by the shield member.

The dispensing end of the nozzle is recessed below the upper end of the shield, from 1/32 inch to ½ inch, preferably 1/16 inch to 3/16 inch.

The shield member can be cup-shaped or thimble-shaped or be comprised of a two or more fingers with the nozzle recessed within the confines of said shield member or be comprised of two fingers joined to form a portion of the cup or thimble shaped shield. The shield may also be a fraction of a cup or thimble, that is, a cup or thimble with portions cut away. The edges of the cup- or thimble-shaped shield or the ends of the fingers need not be of a uniform height.

The shield is small, with a diameter of ¼ inch to 1 inch, not to exceed the diameter of the eye. In the case where the invention consists of a plurality of fingers, or two or more fingers joined to form a portion of the cup or thimble-shaped shield, the diameter is that of the circle which would be formed by joining the fingers. The shield is not intended to come in contact with the eye or with any part of the face. Preferably, the shield has a diameter of ¼ inch to ⅜ inch.

The shield member can be an integral part of the novel dropper tip or can be a separate unit that can be added to or removed from the dispensing device. In either case the material of manufacture of the shield member is not critical but is usually of a plastic material and usually of a deformable plastic.

In one class of embodiments of this invention, the shield is an integral part of the dropper tip. The shield cannot be added or removed and, therefore, must always be used.

In a subclass of embodiments of this invention, two or more fingers are joined to form a portion of the cup- or thimble-shaped shield.

Another embodiment of this invention provides for a cap to fit around and over the shield. A protrusion inside the top of the cap prevents the outflow of liquid from the nozzle and allows for convenient transportation of the device in a handbag or pocket.

Accordingly, it is an object of this invention to provide a dropper tip for a fluid dispensing device, said dropper tip having a recessed nozzle, operable without the limitations presented in the prior art.

It is another object of this invention to provide a cap for said tip.

It is yet another object of this invention to provide a dropper tip for a dispensing device with a recessed nozzle operable by a patient in need of ophthalmic medication free from contaminants.

Additional objects of this invention will be apparent to persons of ordinary skill in the art upon reading the following detailed description and appended claims and upon reference to the accompanying drawings.

BRIEF DESCRIPTION OF THE DRAWINGS

For a more complete understanding of the invention, reference should be made to the embodiments illustrated in greater detail in the accompanying drawings and described below by way of example of the invention.

In the drawings.

Figure 1:
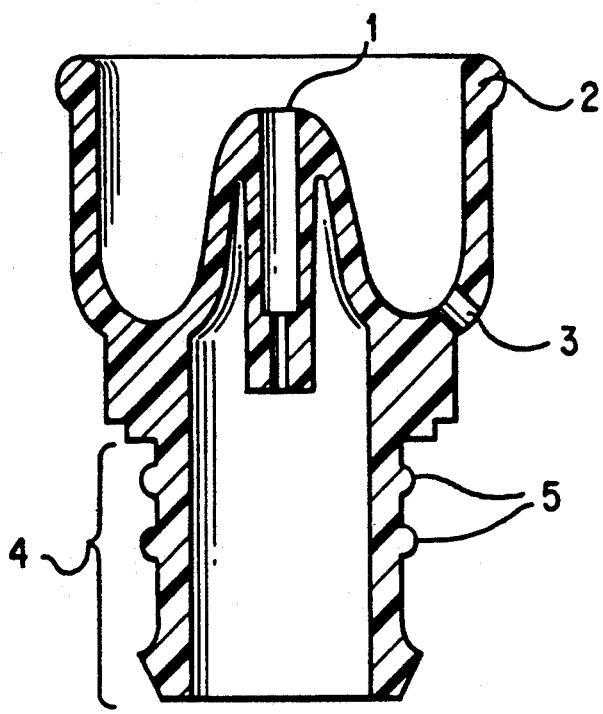
FIG. 1. is a cross-sectional view of the dropper tip, being shown prior to attachment to the body of a fluid-dispensing device.

It should be understood that the drawings are not necessarily to scale and that the embodiments are sometimes illustrated by graphic symbols, phantom lines, diagrammic representations and fragmentary views. In certain instances, details which are not necessary for an understanding of the present invention or which render other details difficult to perceive may have been omitted. It should be understood, of course, that the invention is not necessarily limited to the particular embodiments illustrated herein, and that optimum dimensional relationships include variations which are readily apparent and obvious to one skilled in the art and that all equivalent relationships to those illustrated in the drawings and described in the specification are intended to be encompassed by the present invention.

DETAILED DESCRIPTION OF THE DRAWINGS

Figure 2:
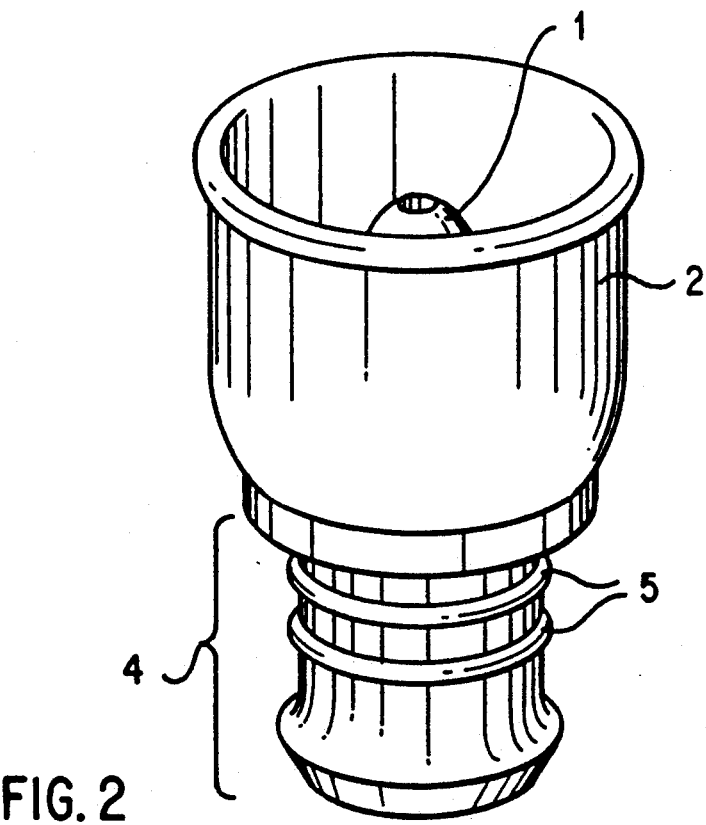
FIG. 2. is a perspective view of the dropper tip of FIG. 1, viewed from slightly above.

FIGS. 1 and 2 depict two views of an embodiment of the recessed dropper tip of this invention which includes a tip, consisting of a nozzle 1, and a shield member 2. From either view, it is apparent that the upper rim of the shield 2 extends beyond the dispensing end 17 of the nozzle 1, functioning to prevent the nozzle from contaminating and/or damaging surface contact. This embodiment includes a drainage hole 3 through which excess fluid, accumulating on the nozzle of elsewhere, can drip out. The stem 4 of the tip has several upraised rings 5 on the exterior to facilitate attachment and sealing to existing dropper bottles.

An entire product comprising the novel tip of this invention would consist of the stem 4 being sealed onto the upper rim of a bottle filled with the fluid to be dispensed. Any suitable means of impermeable attachment may be used to attach the tip to the filled bottle. The bottle may be of any shape, although a preferred shape is cylindrical with sides sloping inward toward the top rim, for ease and completeness of dispensing.

Figure 3:
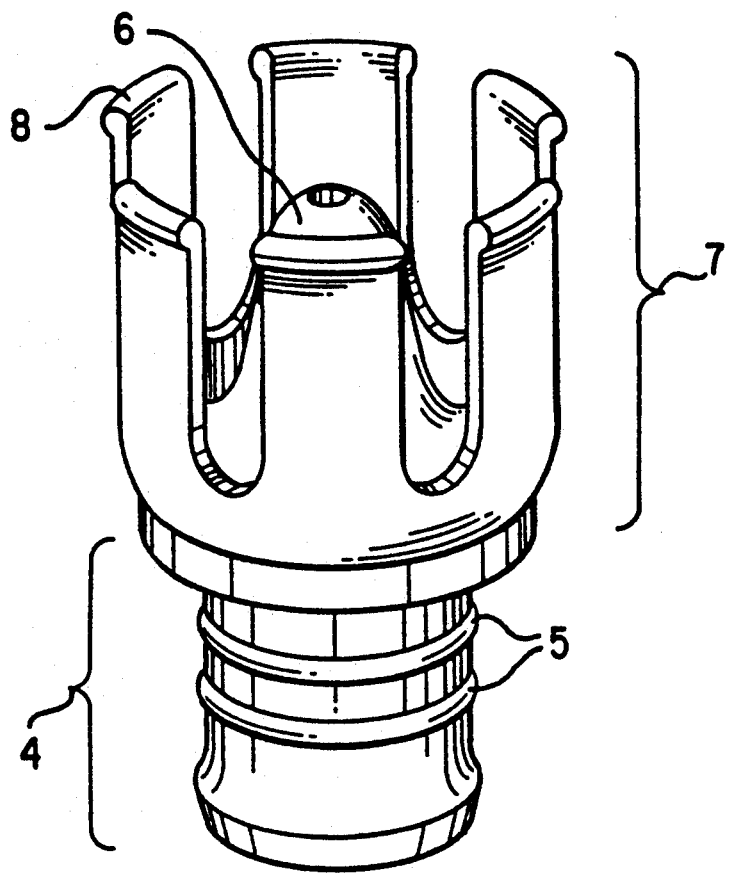
FIG. 3. is a perspective view of an alternative embodiment of the invention, wherein the shield consists of a plurality of fingers.

Illustrated in FIG. 3 is an alternative embodiment of the invention wherein the shield 7 consists of a plurality of fingers 8, preferably from two to ten, most preferably from two to six. The fingers must extend beyond the top of the dispensing nozzle 6 so that the nozzle is recessed within the confines of the shield.

Figure 4:
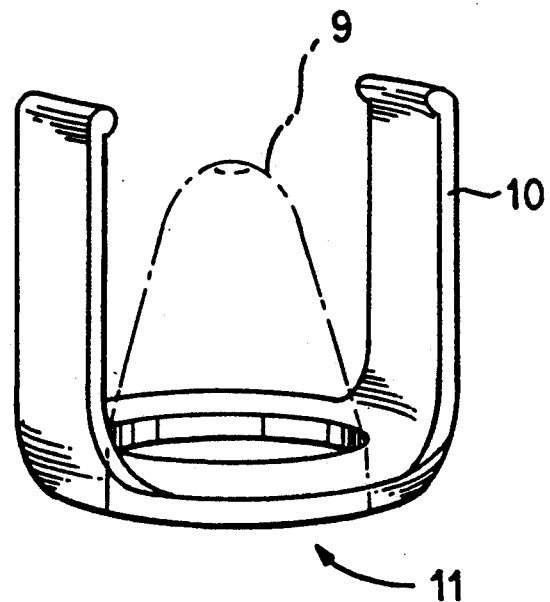
FIG. 4. is a perspective view of an alternative embodiment of the invention comprising the shield only which can be added to or removed from existing dropper bottles, wherein the shield member consists of two fingers, here shown attached to a dropper bottle.
Figure 5:
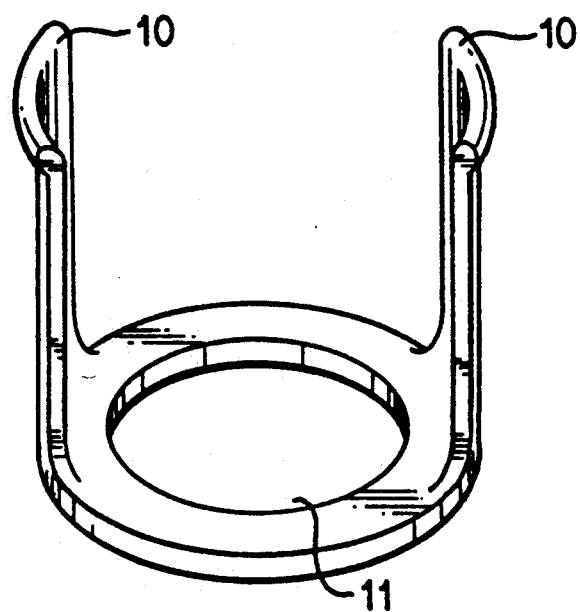
FIG. 5. is a perspective view of the invention of FIG. 4, shown removed from the dropper bottle.

FIGS. 4 and 5 depict an alternative embodiment of the invention, wherein the shield 10 consists of a plurality of fingers (here, two) and an aperture 11 to permit adaptation to an existing dispensing device. In FIG. 4, the nozzle 9 from an existing ophthalmic device is depicted with a broken line. The rim of the protective shield 10 projects beyond the dispensing tip of the nozzle of standard bottles manufactured for this purpose. The shield can be locked onto the nozzle by means such as an undercut along the upper surface of the aperture 11, or other obvious and known means.

Figure 6:
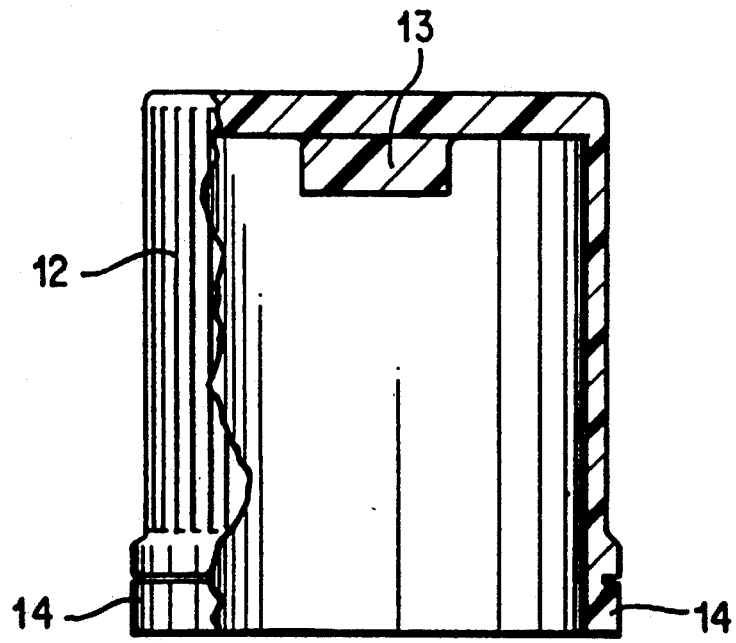
FIG. 6. is a cross sectional view of a cap for the embodiment of FIG. 1.

A cap for the novel dropper tip of this invention is illustrated in FIG. 6. It is shown to have grooves 12 around the circumference to facilitate handling. The interior surface of the top of the cap is shaped to accommodate the shape of the shield and nozzle. The cap has a protrusion 13 in the center which is meant to press firmly on the dispensing end of the nozzle when the cap is in place, thereby preventing leakage if the bottle were inadvertently inverted. The cap also includes a break-away ring 14 at the bottom rim to prevent tampering, although this feature is not essential.

Figure 7:
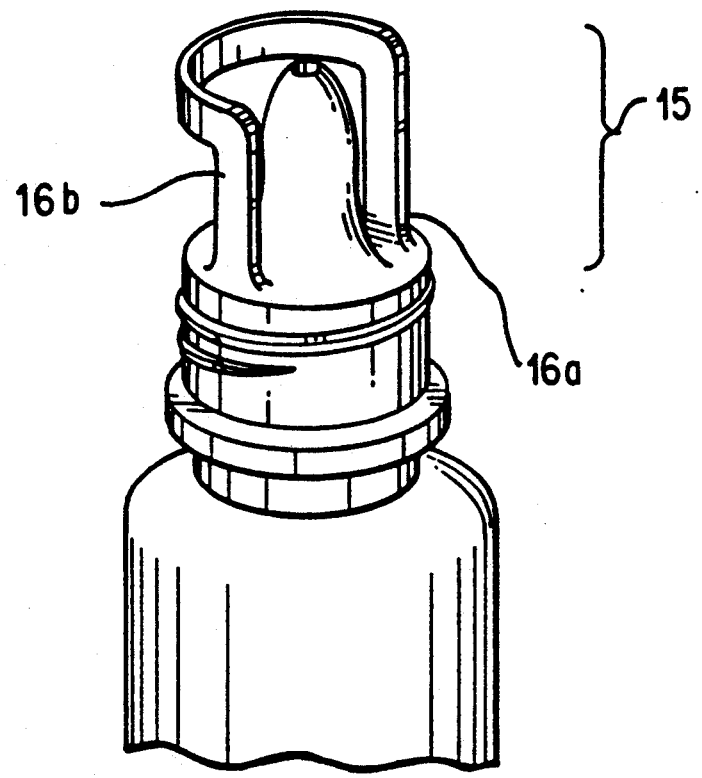
FIG. 7. is a perspective view of another embodiment of the invention comprising an integral shield formed from two fingers joined to form a portion of the thimble-shaped shield. This view depicts the dropper tip attached to the bottle of a dispensing device.

FIG. 7 illustrates anpreferred embodiment of the present invention wherein the shield 15 is an integral part of the dropper tip. The shield 15 is formed from two upwardly projecting fingers 16a and 16b whose upper ends 18a and 18b are joined to form a semicircular portion 19 of the thimble-shaped shield. The dropper tip is shown attached to the bottle of a dispensing device. Alternatively, this may be described as a thimble which has been cut away.

It is to be understood that the present invention has been described above purely by way of example and that modifications of detail can readily be made thereto within the scope and spirit of the invention.

What is claimed is:

1. A dropper tip comprising a nozzle having a dispensing end for dispensing drops and a stem for attachment to a dropper bottle, said tip having a shield member formed from two upwardly projecting fingers projecting from a top of the stem, said fingers being joined at their upper ends above the dispensing end to form a semicircle on only one side of a plane formed by the fingers, the semicircle having a diameter of less than ⅝ of an inch to protect the nozzle from contamination.

* * * * *